(12) United States Patent
Mupende et al.

(10) Patent No.: US 10,359,347 B2
(45) Date of Patent: *Jul. 23, 2019

(54) DEVICE FOR DETECTING THE REPLACEMENT STATE OF WEAR OF A HIGH-STRENGTH FIBER ROPE DURING USE IN LIFTING GEAR

(71) Applicant: Liebherr-Components Biberach GmbH, Biberach an der Riss (DE)

(72) Inventors: Ilaka Mupende, Neu-Ulm (DE); Horst Zerza, Biberach an der Riss (DE)

(73) Assignee: Liebherr-Components Biberach GmbH, Biberach an der Riss (DE)

( * ) Notice: Subject to any disclaimer, the term of this patent is extended or adjusted under 35 U.S.C. 154(b) by 135 days.

This patent is subject to a terminal disclaimer.

(21) Appl. No.: 14/915,605

(22) PCT Filed: Jul. 24, 2014

(86) PCT No.: PCT/EP2014/002029
§ 371 (c)(1),
(2) Date: Feb. 29, 2016

(87) PCT Pub. No.: WO2015/028113
PCT Pub. Date: Mar. 5, 2015

(65) Prior Publication Data
US 2016/0216183 A1    Jul. 28, 2016

(30) Foreign Application Priority Data
Aug. 27, 2013   (DE) .................. 10 2013 014 265

(51) Int. Cl.
*G01N 3/24* (2006.01)
*B66C 15/00* (2006.01)
(Continued)

(52) U.S. Cl.
CPC ............... *G01N 3/24* (2013.01); *B66C 15/00* (2013.01); *B66D 1/54* (2013.01); *G01L 5/04* (2013.01);
(Continued)

(58) Field of Classification Search
CPC .... B66D 1/58; G01M 5/0041; G01M 99/007; G01L 5/04; G01N 3/24
See application file for complete search history.

(56) References Cited

U.S. PATENT DOCUMENTS 3,176,510 A * 4/1965 Kimmell .................. G01L 5/08
73/862.454
3,572,596 A * 3/1971 Dykmans ................ B28B 21/64
242/438.1
(Continued)

FOREIGN PATENT DOCUMENTS

CN    1134484 A    10/1996
CN    1256412 A    6/2000
(Continued)

OTHER PUBLICATIONS

Document U—English Translation of DE 202011001846 (Jan. 11, 2017).*
(Continued)

*Primary Examiner* — Harshad R Patel
*Assistant Examiner* — Tran M. Tran
(74) *Attorney, Agent, or Firm* — McCoy Russell LLP

(57) ABSTRACT

An arrangement for detecting the discard state of a high-strength fiber rope when used on such hoists, with a device for determining at least one rope parameter and an evaluation unit for evaluating the rope parameter, and providing a discard signal depending upon the evaluation of the rope parameter. The determination device comprises bending stiffness determination means for determining the bending
(Continued)

stiffness of the rope, whereby the evaluation unit provides the discard signal depending on the determined bending stiffness of the rope.

18 Claims, 2 Drawing Sheets

(51) Int. Cl.
*B66D 1/54* (2006.01)
*G01M 5/00* (2006.01)
*G01L 5/04* (2006.01)
*G01N 3/08* (2006.01)

(52) U.S. Cl.
CPC ............ *G01M 5/0058* (2013.01); *G01N 3/08* (2013.01); *G01N 2203/028* (2013.01)

(56) References Cited

U.S. PATENT DOCUMENTS

| | | | | |
|---|---|---|---|---|
| 3,664,182 A * | 5/1972 | Butler | G01N 3/22 | 73/794 |
| 3,826,321 A * | 7/1974 | Rigney | B66C 13/16 | 177/145 |
| 3,832,899 A * | 9/1974 | Nicolau | G01L 5/08 | 73/862.194 |
| 3,916,686 A * | 11/1975 | Lear | G01M 99/007 | 374/49 |
| 4,055,137 A * | 10/1977 | Motai | B63B 21/00 | 114/230.21 |
| 4,163,126 A * | 7/1979 | Van Mastrigt | B65H 59/40 | 200/61.13 |
| 4,171,640 A * | 10/1979 | van Mastrigt | G01L 5/107 | 73/862.451 |
| 4,241,616 A * | 12/1980 | Mastrigt | G01L 5/04 | 73/862.451 |
| 4,287,759 A * | 9/1981 | Cooper | G01L 5/107 | 254/273 |
| 4,305,513 A * | 12/1981 | Voelz | B66D 1/54 | 212/276 |
| 4,368,824 A * | 1/1983 | Thomasson | B66C 23/905 | 212/278 |
| 4,480,487 A * | 11/1984 | Kunzfeld | G01L 5/08 | 73/862.453 |
| 4,487,068 A * | 12/1984 | Hawkins | G01N 29/14 | 73/159 |
| 4,534,228 A * | 8/1985 | Burbank, Jr. | G01L 5/08 | 73/862.454 |
| 4,562,743 A * | 1/1986 | Bonine | G01B 5/30 | 73/158 |
| 4,587,855 A * | 5/1986 | Yamada | G01L 5/10 | 73/862.451 |
| 4,615,509 A * | 10/1986 | Biass | B66D 3/006 | 254/228 |
| 4,624,450 A * | 11/1986 | Christison | B66D 1/52 | 254/272 |
| 4,846,000 A * | 7/1989 | Steinseifer | G01L 5/04 | 340/668 |
| 4,895,079 A * | 1/1990 | Beatty | B66D 1/50 | 104/174 |
| 4,906,981 A * | 3/1990 | Nield | B66C 23/905 | 212/278 |
| 4,914,960 A * | 4/1990 | Kordahi | G01L 5/10 | 73/862.451 |
| 4,989,450 A * | 2/1991 | Shoberg | G01L 5/10 | 73/1.15 |
| 4,992,778 A * | 2/1991 | McKeen | B66C 15/00 | 116/212 |
| 5,160,055 A * | 11/1992 | Gray | B66C 23/90 | 212/278 |
| 5,251,492 A * | 10/1993 | Nowag | G01L 5/04 | 73/862.391 |
| 5,277,406 A * | 1/1994 | Knight | B66D 1/50 | 114/213 |
| 5,454,272 A * | 10/1995 | Miller | G01L 5/042 | 73/862.391 |
| 5,728,953 A * | 3/1998 | Beus | G01G 3/12 | 73/862.392 |
| 5,817,947 A * | 10/1998 | Bergerus | G01B 7/107 | 73/826 |
| 5,834,942 A | 11/1998 | De Angelis | | |
| 5,890,564 A * | 4/1999 | Olsen | B66B 7/123 | 187/250 |
| 5,965,827 A * | 10/1999 | Stanley | G01L 5/10 | 73/862.391 |
| 6,041,666 A * | 3/2000 | MacKarvich | G01L 5/06 | 73/828 |
| 6,134,974 A * | 10/2000 | Grover | G01L 5/10 | 73/862.451 |
| 6,215,315 B1 * | 4/2001 | Maejima | G11B 15/6835 | 324/539 |
| 6,247,359 B1 | 6/2001 | De Angelis | | |
| 6,644,583 B2 * | 11/2003 | Schmidt | B65H 59/22 | 242/419.4 |
| 6,658,783 B1 * | 12/2003 | Yamanaka | A01K 97/00 | 43/25 |
| 6,901,818 B1 * | 6/2005 | Cheung | G01L 5/10 | 114/230.1 |
| 6,923,065 B2 * | 8/2005 | Smith | B66B 7/1215 | 324/535 |
| 7,066,036 B2 * | 6/2006 | Ochovo | B66B 1/3484 | 73/862.472 |
| 7,134,645 B1 * | 11/2006 | Johnson | B66D 1/741 | 254/338 |
| 7,424,832 B1 * | 9/2008 | Nunnelee | G01L 5/107 | 73/862.472 |
| 7,478,563 B2 * | 1/2009 | Weisman | G01L 5/042 | 73/786 |
| 8,069,737 B2 * | 12/2011 | Hanoun | G01L 5/106 | 73/862.474 |
| 8,073,653 B2 * | 12/2011 | Suzuki | G07C 3/00 | 702/181 |
| 8,408,076 B2 * | 4/2013 | McElroy | G01G 19/18 | 73/862.471 |
| 8,707,757 B2 * | 4/2014 | Kral | G01M 99/007 | 73/12.13 |
| 8,766,812 B2 * | 7/2014 | Pereira | B66B 5/12 | 340/668 |
| 8,931,350 B2 * | 1/2015 | Mupdende | G01N 3/08 | 73/829 |
| 9,016,486 B2 * | 4/2015 | Noll | B66C 19/00 | 212/312 |
| 9,290,909 B2 * | 3/2016 | Brenny | E02F 3/36 | |
| 9,335,318 B2 * | 5/2016 | Ilaka | B66C 13/16 | |
| 9,527,675 B2 * | 12/2016 | Tout | B65G 23/44 | |
| 9,873,597 B2 * | 1/2018 | Mupende | B66C 15/00 | |
| 2003/0052695 A1 * | 3/2003 | Smith | B66B 7/1215 | 324/535 |
| 2008/0265932 A1 * | 10/2008 | Shibata | G01R 31/2887 | 324/756.05 |
| 2014/0027401 A1 | 1/2014 | Ilaka et al. | | |
| 2015/0314997 A1 * | 11/2015 | Petrak | B66C 13/46 | 212/278 |
| 2016/0221800 A1 * | 8/2016 | Mupende | G01N 3/22 | |
| 2016/0236913 A1 * | 8/2016 | Ilaka | B66C 13/16 | |

FOREIGN PATENT DOCUMENTS

| | | | | |
|---|---|---|---|---|
| CN | 201548517 U | 8/2010 | | |
| CN | 102564875 A | 7/2012 | | |
| DE | 8702674 U1 | 6/1988 | | |
| DE | 102009056068 A1 | 6/2011 | | |
| DE | 202011001846 U1 * | 4/2012 | ............ | B66C 13/16 |
| JP | H07181167 A | 7/1995 | | |
| JP | H09012271 A | 1/1997 | | |

(56) References Cited

FOREIGN PATENT DOCUMENTS

JP  2001192183 A  7/2001
WO  2012100938 A1  8/2012

OTHER PUBLICATIONS

ISA European Patent Office, International Search Report Issued in Application No. PCT/EP2014/002029, dated Oct. 2, 2014, WIPO, 6 pages.
State Intellectual Property Office of the People's Republic of China, Office Action and Search Report Issued in Application No. 201480058915.6, dated Dec. 15, 2016, 15 pages. (Submitted with Partial Translation).
Yao, W. et al., "The Measuring of the Bending Stiffness of Steel Wires," Mechanics and Practices, vol. 20, No. 2, Apr. 15, 1998, 3 pages. (Cited in NPL 2, Office Action and Search Report issued in Application No. 201480058915.6, dated Jan. 29, 2018, which is submitted herewith along with its English translation as explanation of relevance).
State Intellectual Property Office of the People's Republic of China, Office Action and Search Report Issued in Application No. 201480058915.6, dated Jan. 29, 2018, 17 pages. (Submitted with translation of Office Action).
Japan Patent Office, Office Action Issued in Application No. 2016-537152, dated Apr. 10, 2018, 6 pages.

* cited by examiner

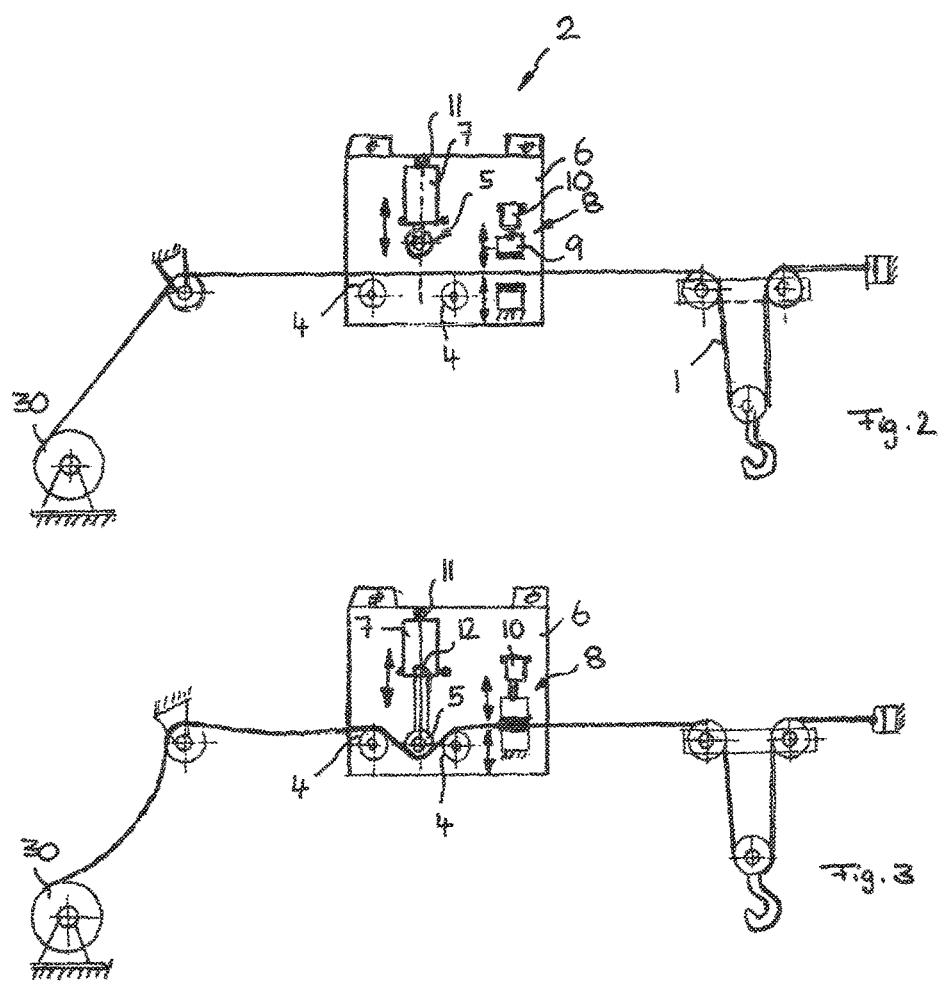

ical Field

DEVICE FOR DETECTING THE REPLACEMENT STATE OF WEAR OF A HIGH-STRENGTH FIBER ROPE DURING USE IN LIFTING GEAR

CROSS REFERENCE TO RELATED APPLICATIONS

The present application is a U.S. National Phase of International Patent Application Serial No. PCT/EP2014/002029, entitled "Device for Detecting the Replacement State of Wear of a High-Strength Fibre Rope During Use in Lifting Gear," filed on Jul. 24, 2014, which claims priority to German Patent Application No. 10 2013 014 265.2, filed on Aug. 27, 2013, the entire contents of each of which are hereby incorporated by reference in their entirety for all purposes.

TECHNICAL FIELD

The present invention relates generally to hoists such as cranes which instead of steel wire ropes use high-strength fibre ropes. The invention relates in particular to an arrangement for detecting the discard state of a high-strength fibre rope when used on such hoists, with a detection means for detecting at least one rope parameter and an evaluation unit for evaluating the rope parameters, and providing a discard signal depending upon the evaluation of the rope parameter.

BACKGROUND AND SUMMARY

Instead of steel wire ropes that have been used successfully on cranes for many years, it is recently being tried to use high-strength fibre ropes made of synthetic fibres such as aramid fibres (HMPA), aramid/carbon composites, highly modular polyethylene fibres (HMPE) or poly(p-phenylene.2,6-benzobisoxazole) fibres (PBO). The advantage of such high-strength fibre ropes is their low weight. At equal rope diameters and equal or higher tensile strengths, such high-strength fibre ropes are clearly lighter in weight than comparable steel wire ropes. In particular for high cranes with accordingly long rope lengths, this results in a major weight reduction reflected in the dead weight of the crane leading to higher payloads for an otherwise unchanged crane design.

However, a disadvantage of such high-strength fibre ropes is their breaking behaviour, i.e. their failure without any distinct long-term prior warning. While wear is clearly indicated with steel wire ropes, showing failure long in advance, for example when individual steel wires break and splice open, which is easily detected, high-strength fibres show few signs of excess splicing that could be detected with the naked eye and that would show long before their actual failure. They therefore require intelligent monitoring measures to allow the early detection of when the discard state of high-strength fibre ropes will occur.

It is known from WO 2012/100938 A1 to detect the discard state of a high-strength fibre rope by testing various rope discard criteria which change over the time in which a rope is used and under stress. Here, the rope diameter, the shear stress stiffness measured by the cross-sectional changes resulting when the rope is pinched, and by the number of completed stress cycles. However, the informative value of these individual discard criteria is limited, which means that the interaction of these discard criteria must be monitored and evaluated in a rather complex monitoring process before the discard state can actually be detected with reliability.

Based on this, it is the object of the present invention to provide an improved device for detecting the discard state of high-strength fibre ropes which avoids the disadvantages of the prior art and advantageously develops it further. Preferably, a simple but reliable and precise detection of the discard state is to be achieved which economically utilizes the remaining service life if the fibre rope without jeopardizing safety, and which can be used on construction machinery with simple detection means functioning reliably even under heavy-duty working conditions.

According to the invention, the above object is achieved with a device and a crane. Preferred embodiments of the invention are the subject of the sub-claims.

It is therefore suggested to monitor the rope's bending stiffness and to determine the discard state by means of the rope's bending stiffness. According to the invention, the evaluation unit comprises bending stiffness determination means for determining the rope's bending stiffness, whereby the evaluation unit provides the discard signal depending on the determined bending stiffness of the rope. While steel wire ropes do not show significant changes in bending stiffness depending on the rope's service life, this is different with high-strength fibre ropes. The filaments which are still flexible at the beginning of the rope's use, are made harder and the rope is made stiffer by the tensile stress and the bending stress. This increase in the rope's bending stiffness is easy to measure, which means that the discard state can be determined reliably and precisely by the rope's monitored bending stiffness. It shows that rope twisting tests with a new rope show a rather low bending stiffness while ropes driven to the breaking point show a very high bending stiffness in the end due to prolonged and severe stress, namely many times that of the rope's original state. This increase rises continuously with the cycles-to-failure rate, reaching the highest point when the rope breaks, which means that the evaluation unit can determine the discard state relatively easily.

In the further development of the invention, the bending stiffness determination means can comprise two rope support elements spaced apart from each other and at least one shear force stamp for applying pressure to the rope with a shear force, whereby the shear force stamp and/or the rope support elements can be moved across the lengthwise direction of the rope such that the rope is subjected to curvature. Advantageously, a laterally movable shear force stamp can be arranged between the two rope support elements spaced apart from each other, and essentially across a connecting line through the two rope support elements, whereby the movability can be such that the pressure head or engagement head of the shear force stamp can be moved toward the said connecting line and advantageously across this connecting line. In principle it would also be possible to arrange the said shear force stamp not between the two rope support elements but on a side of the two rope support elements, especially in the area of an extension of the said connecting line beyond the two rope support elements, such that the shear force stamp acts upon the rope like a projecting flexure beam.

In the above mentioned arrangement of the shear force stamp between the two rope support elements, the arrangement is advantageously such that the two rope support elements are arranged on one side of the rope while the shear force stamp is arranged on the opposite side of the rope.

In a further development of the invention, the shear force stamp and/or the rope support elements can be provided with a dynamometer and/or a travel meter for measuring the shear force and/or the travel of the shear force stamp and/or the rope support elements applied across the lengthwise direction of the rope to be tested. Instead of such a travel meter, a deflection sensor could be provided which measures the deflection or displacement of the rope across the lengthwise direction of the rope.

The rope's bending stiffness can be determined with the bending stiffness determination means by means of the deflection of the rope that can be achieved with a predetermined shear force and/or with the shear force required for a predetermined deflection. In a further development of the invention, these two determination criteria can also be used in combination with each other, in particular such that it is determined what force is required for a predetermined deflection and what deflection occurs at a predetermined shear force, thus taking into account any non-linearities that may occur with regard to shear stress stiffness.

In an advantageous further development of the invention, the rope is only supported by the said rope support elements and/or by the shear force stamp without absorbing bending moments or torques that might occur. In particular, the rope support elements and the shear force stamp are designed such that no moment resistance is set against the twisting or bending of the rope. For example, the rope support elements and the shear force stamp can form unilateral supporting points or planes which essentially absorb forces only across the rope's lengthwise direction but do not transfer any bending moments to the rope.

Not to falsify the measuring of the rope's bending stiffness by stresses acting upon the rope from tensile forces, the bending stiffness determination means comprises a tensile force adjuster which always establishes the same tensile force conditions on the rope for repetitive bending stiffness measurements. In particular, the said tensile force adjuster can comprise a tensile force release means which essentially completely releases the rope of tensile forces when the rope's bending stiffness is determined.

In principle, the said tensile force release means can have different designs. In an advantageous further development of the invention, the tensile force release means can comprise holding means for holding the rope in lengthwise direction, preferably at least one rope clamp to clamp the rope, in particular to absorb hoist loads at the lifting hook, and which releases the rope section to be tested for the rope's bending stiffness. In particular, the said rope clamp can be associated with the rope on a side of the bending stiffness determination means facing away from the rope drum, such that when the rope is pinched, a nearly complete tensile stress release can be achieved for the rope section to be tested by releasing the clamped rope or by unwinding the rope drum. Corresponding control means can control the rope drum to unwind it for a predetermined piece or to activate it in the direction of lowering the load, such that rope slack is produced between the rope clamp and the rope drum.

In principle, the evaluation unit for providing a discard signal can work in various ways, for example by monitoring changes in the rope's bending stiffness and/or by monitoring the absolute bending stiffness. In particular, the said evaluation unit can be designed such that a discard signal is provided when the rope's bending stiffness and/or its change exceeds a certain threshold value.

For example, one or more reference measurements can be conducted on a new rope such that the percentage change in the rope's bending stiffness that occurs during operation can be compared with a threshold value for change or that the discard signal is provided when this threshold value is exceeded or reached. In particular, the discard signal can be provided when the rope's bending stiffness rises above a still tolerable threshold value. As an alternative or in addition, the monitored bending stiffness which is constantly or periodically determined during operation can be compared with an absolute threshold value that is provided by the manufacturer for a certain type of rope or for a specific rope, and that the discard signal is then provided when this threshold value is exceeded. Also as an alternative or in addition, the discard signal can be provided when the measured change in the rope's bending stiffness is too rapid and/or too slow, i.e. when the change frequency of bending stiffness exceeds or falls below a threshold value. The speed of change in time can be the speed of change in the number of load cycles which, for example, can be detected with a load cycle counter and considered by the evaluation unit. As an alternative or in addition, the speed of change can also only be taken into account by the number of measurements of the rope's bending stiffness, for example by providing a discard signal when the change in the rope's bending stiffness detected after a certain number of measurements, for example after the tenth measurement, exceeds the threshold value predetermined for that purpose.

The discard signal can simply be indicated to the crane operator, for example acoustically and/or visually, or it can be used to stop the rope drive.

In an advantageous further development of the invention, the bending stiffness determination means can be firmly installed in the rope drive of the hoist such that the rope's bending stiffness can be constantly monitored during operation, i.e. in the operational state of the hoist, without the necessity of having to convert the hoist into a special test modus. As an alternative or in addition, the bending stiffness determination means can also be provided as a detachable unit that can be used in different hoists.

In an advantageous further development of the invention, the bending stiffness determination means are arranged in a rope section of the rope drive which is subject to most bending changes. In the hoisting rope of a tower crane, for example, this can be a rope section intended to run around the deflection pulleys on the trolley and the deflection pulleys on the lifting hook. Depending on the design of the hoist and the course or reeving system of the rope, these can be various rope sections.

BRIEF DESCRIPTION OF FIGURES

Below, the invention is described in more detail by means of a preferred embodiment and with reference to the drawings.

FIG. 2 shows a schematic view of the rope drive of the crane shown in FIG. 1 and of the bending stiffness determination means associated with this rope drive, whereby the determination means are shown in an initial state in which the rope is still unstressed and can be wound and unwound in crane operations.

FIG. 3 shows a schematic view of the rope drive and the bending stiffness determination means associated with the rope drive, similar to FIG. 2, whereby the bending stiffness determination means are shown in an active test mode in which the rope is pinched and released from tensile stress, but subjected to bending stress.

DETAILED DESCRIPTION

Figure 1:
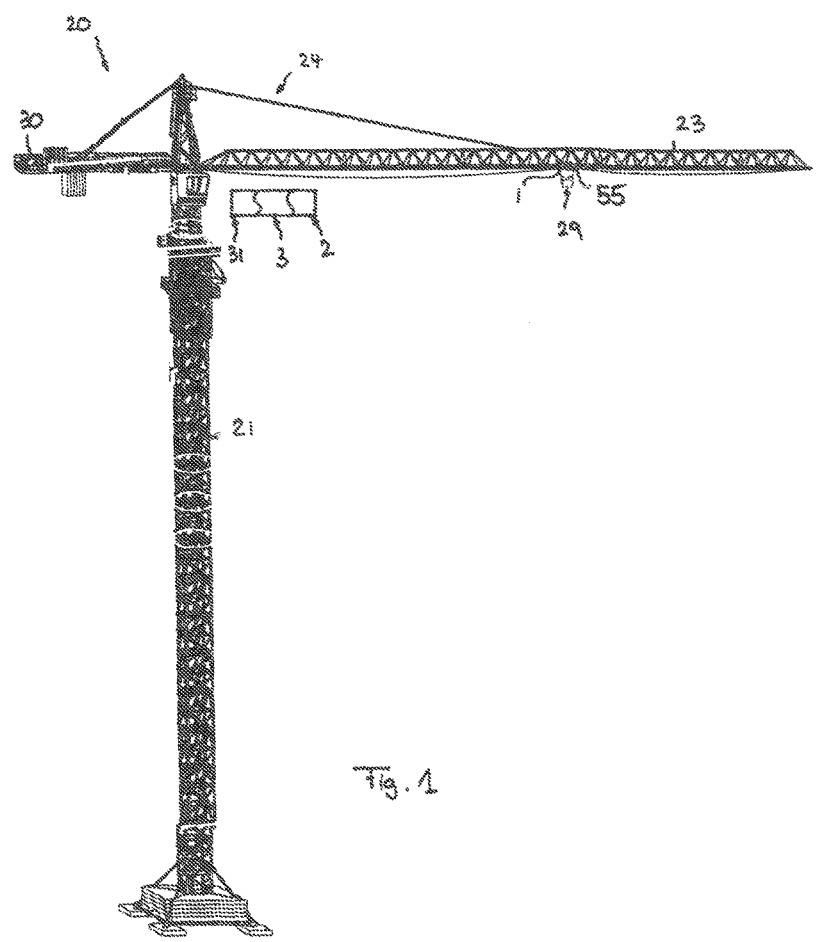
FIG. 1 shows a schematic view of a hoist according to the invention in the form of a tower crane according to an advantageous embodiment of the invention, whose hoisting rope and/or bracing ropes can be designed for the luffable jib as fiber ropes.

FIG. 1 shows as an example a hoist according to an advantageous embodiment of the invention in the form of a top-slewing crane 20 whose tower 21 is mounted on a carriage or fixed base. Linked to tower 21 in a previously known manner is a boom 23 braced by bracing 24. The said bracing 24 can be rigid, for example in the form of bracing rods, but also adjustable in the form of a rope reeving that can be changed in length via a bracing winch 25 such that the working angle of boom 23 can be changed.

As shown in FIG. 1, the tower crane 20 can be provided with a trolley boom. A trolley 55 is installed horizontally on the said crane in operating position, in particular on its horizontally oriented boom 23, whereby the said trolley 55 can, for example, be moved via a trolley rope which can be guided via deflection pulleys at the boom tip.

The tower crane also comprises a hoisting rope 1 that can be lowered via deflection pulleys from the boom tip where it is connected with a crane hook 29 or in the version according to FIG. 1 can run via the said movable trolley 55 and the deflection pulleys provided there, and can be connected with the crane hook 29. In both cases, the said hoisting rope 1 runs on a hoist winch 30.

The said hoisting rope 1 [A1] and/or the bracing rope can be designed as fibre ropes which can consists of synthetic fibres such as aramid fibres or fibres made from a mixture of aramid and carbon.

To monitor or detect the parameters of the said fibre rope relevant to its discard state, a detection means is provided that can be arranged on the crane and which together with an evaluation unit 3, which evaluates the acquired parameters, can be connected with or integrated in the electronic crane control unit 31.

As FIGS. 2 and 3 show, the bending stiffness determination means 2 advantageously comprises two rope support elements 4 which, for example, can be designed as rigid slide bearing jaws or as a rope pulley spaced apart from each other, such that they support the rope 1 in a rope section across the rope's lengthwise direction. Between the spaced-apart rope support elements 4, a shear force stamp 5 is provided which can apply a shear force to rope 1 across the rope's lengthwise direction. Advantageously, the shear force stamp 5 on the one hand and the two rope support elements 4 on the other hand are arranged on opposite sides of rope 1, and they can be mounted together on a bearing plate 6 or another suitable bearing body.

As FIGS. 2 and 3 show, the shear force stamp 5 can be moved across the rope's lengthwise direction such that the rope abutting on the rope support elements 4 is subjected to deflection. In particular, the shear force stamp 5 can be moved in the area of a connecting line between the two rope support elements 4 and beyond this connecting line. A control actuator 7, for example in the form of a pressure cylinder or an electric motor with control spindle can be provided to move the shear force stamp 5.

The head of the shear force stamp 5—similar to the rope support elements 4—can be designed as a slide bearing jaw or advantageously as a rope trolley to prevent introducing forces into rope 1 in lengthwise direction.

To relieve rope 1 of tensile forces for the measuring of bending stiffness, a tensile force release means 8 comprises a rope clamp 9 that can be activated by a control actuator 10, for example in the form of a pressure cylinder, to clamp and hold the rope.

Preferably, the said rope clamp 9 is arranged on the lifting hook side or on the side of bending stiffness determination means 2 facing away from the rope drum such that loads and rope weight forces acting upon the lifting hook cannot induce rope pull in the rope section to be tested.

The tensile force release means 8 also comprises control means for controlling the rope drum such that rope 1 of the rope clamped with rope clamp 9 is wound off a piece to create rope slack between the rope drum and the rope clamp 9, i.e. to ensure that the rope is not subjected to tensile force there.

Advantageously, the bending stiffness of rope 1 can be detected by means of the following steps:
  First, the rope is moved into the position to be measured, for which the hoist position measuring means of the lifting hook can be used. In particular, the rope section is moved into bending stiffness determination means 2 which is intended to be subjected to most bending changes and/or load cycles. If need be, several rope sections can be moved in succession into bending stiffness determination means 2 to determine the bending stiffness in different rope sections.
  The rope is fixed with the clamping arrangement or rope clamp 9.
  Rope 1 is loosened by slightly moving downward from the drum side, thus releasing tension from rope 1.
  The shear force stamp 5 is moved from the stationary position shown in FIG. 1 and toward rope 1 to produce the rope deflection shown in FIG. 3. The bending resistance of the rope is measured. On the one hand, this can comprise measuring the force required to reach a predetermined deflection. As an alternative or in addition, the travel of shear force stamp 5 and/or the lateral deflection of the rope can be measured which occurs when subjected to a predetermined shear force. For that purpose, control actuator 7 and/or the rope support elements 4 can be provided with dynamometers 11 or force sensors and/or travel sensors 12.
  The value of the bending resistance of rope 1 thus determined is stored in the memory of the bending stiffness determination means 2 and compared with an admissible predetermined value.
  After measuring, the bending stiffness determination means 2 are returned to their original stationary state as shown in FIG. 1.
  Then, rope 1 can be moved to test another rope section, repeating the above steps. As an alternative or in addition, the rope can be moved in crane operation when the desired measurements have been completed.
  Moving the rope section for determining torsional stiffness can be automatically programmed or controlled manually by moving to different measuring positions at appropriate intervals over a determined rope length.

The invention claimed is:

1. An arrangement for detecting a discard state of a high-strength fiber rope used on hoists, with
  a hoist winch;
  a crane hook; and
  an evaluation unit positioned between the hoist winch and the crane hook,
    wherein the evaluation unit comprises a bending stiffness determination device for determining the rope's bending stiffness, the bending stiffness determination device including a rope clamp and a shear force stamp, the shear force stamp positioned between the rope clamp and the hoist winch, and wherein the evaluation unit provides a discard signal depending on a determined bending stiffness of the rope, where the rope is clamped via the rope clamp while the bending stiffness of the rope is determined based on an amount of shear force applied by the shear force stamp to an initially unbent section of the rope and based on an amount the rope deflects from unbent responsive to the application of the amount of shear force.

2. The arrangement according to claim 1, wherein the bending stiffness determination device comprises two rope support elements spaced apart from each other and a shear force stamp for applying pressure to the rope with a shear force, whereby the shear force stamp and/or the rope support elements is/are movable across a lengthwise direction of the rope such that the rope is given a curvature.

3. The arrangement according to claim 2, wherein a dynamometer and/or a travel meter is/are associated with the shear force stamp and/or the rope support elements, whereby the rope bending stiffness can be determined with the bending stiffness determination device by means of a deflection achievable with a predetermined shear force and/or by means of the shear force required for a predetermined deflection.

4. The arrangement according to claim 2, wherein the shear force stamp is arranged between the rope support elements, viewed in the lengthwise rope direction.

5. The arrangement according to claim 4, wherein the rope support elements and/or the shear force stamp form unilateral supports on which the rope is freely bendable and/or rotatable, wherein the rope support elements and the shear force stamp comprise rotatable rope pulleys for charging the rope laterally.

6. The arrangement according to claim 2, wherein the rope support elements and/or the shear force stamp form unilateral supports on which the rope is freely bendable and/or rotatable, wherein the rope support elements and the shear force stamp comprise rotatable rope pulleys for charging the rope laterally.

7. The arrangement according to claim 6, wherein the bending stiffness determination device comprises a tensile force release means to clamp the rope and release the rope of tensile forces caused by a load during a bending stiffness test.

8. The arrangement according to claim 1, wherein the rope clamp is included in a tensile force release device to clamp the rope and release the rope of tensile forces caused by a load during a bending stiffness test.

9. The arrangement according to claim 8, wherein the rope clamp for clamping the rope is positioned on a side of the bending stiffness determination device facing away from the hoist winch.

10. The arrangement according to claim 8, wherein the evaluation unit provides the discard signal when the rope bending stiffness and/or its change determined by the bending stiffness determination device exceeds a threshold value.

11. The arrangement according to claim 1, wherein the evaluation unit provides the discard signal when the rope bending stiffness and/or its change determined based on the bending stiffness determination device exceeds a certain threshold value.

12. The arrangement according to claim 1, wherein the bending stiffness determination device comprises rope support elements that position one or more rope sections for a process of determining a rope bending stiffness of the one or more rope sections.

13. The arrangement according to claim 1, wherein the hoist winch comprises a crane.

14. The arrangement according to claim 1, wherein the evaluation unit provides the discard signal responsive to the determined bending stiffness of the rope being greater than a threshold value.

15. A crane, with an arrangement for detecting a discard state of a high-strength fiber rope, comprising:
 a hoist winch;
 a crane hook;
 a carriage or a fixed base coupled with the hoist winch;
 an evaluation unit positioned between the hoist winch and the crane hook, the evaluation unit comprising a bending stiffness determination device for determining a bending stiffness of the rope, the bending stiffness determination including a rope clamp and a shear force stamp, the shear force stamp positioned between the rope clamp and the hoist winch,
 wherein the evaluation unit provides a discard signal depending on the determined bending stiffness of the rope, where the rope is clamped via the rope clamp while the bending stiffness of the rope is determined based on an amount of shear force applied to an initially unbent section of the rope via the shear force stamp and based on an amount the rope deflects from unbent responsive to the application of the amount of shear force.

16. The crane according to claim 15, wherein one or more determination devices are rigidly installed and assigned to a rope drive of the crane or designed as a removable unit such that the determined bending stiffness of the rope can be detected in the crane already equipped for crane operation.

17. The crane according to claim 16, wherein the one or more determination devices are arranged such that a rope section, subjected to most bending changes and/or load cycles, can be tested with the determination devices.

18. The crane according to claim 15, wherein the crane comprises one of a tower crane, a mobile crane, a mobile harbor crane, a ship's crane, or a vehicle boom crane.

* * * * *